(12) United States Patent
Deguchi et al.

(10) Patent No.: US 6,962,809 B1
(45) Date of Patent: Nov. 8, 2005

(54) SUGAR CHAIN SYNTHESIZER

(75) Inventors: Kisaburo Deguchi, Hitachinaka (JP);
Genzo Hirata, Hitachinaka (JP);
Junkichi Miura, Hitachinaka (JP);
Masahito Ito, Hitachinaka (JP);
Shinichiro Nishimura, Sapporo (JP);
Susumu Nishiguchi, Otsu (JP); Atsushi Toda, Tsuruga (JP); Hiroaki Nakagawa, Sapporo (JP); Kuriko Yamada, Sapporo (JP)

(73) Assignees: Hitachi, Ltd., Tokyo (JP); Toyobo Co., Ltd., Osaka (JP)

( * ) Notice: Subject to any disclaimer, the term of this patent is extended or adjusted under 35 U.S.C. 154(b) by 137 days.

(21) Appl. No.: 10/482,626

(22) PCT Filed: Jul. 1, 2002

(86) PCT No.: PCT/JP02/06642

§ 371 (c)(1),
(2), (4) Date: Feb. 10, 2004

(87) PCT Pub. No.: WO03/004597

PCT Pub. Date: Jan. 16, 2003

(30) Foreign Application Priority Data

Jul. 2, 2001 (JP) ......................................... 2001-200290
May 10, 2002 (JP) ......................................... 2002-134871

(51) Int. Cl.[7] .............................................. C12M 1/34
(52) U.S. Cl. .............................. 435/288.7; 435/289.1; 422/70; 422/82.05; 422/131; 422/212; 422/234
(58) Field of Search ................................. 422/70, 82.05, 422/131, 212, 234; 435/288.6, 288.7, 289.1

(56) References Cited

U.S. PATENT DOCUMENTS 5,856,082 A * 1/1999 Aebersold et al. ............. 435/4
6,329,182 B1 * 12/2001 Pedersen et al. ............. 435/96

FOREIGN PATENT DOCUMENTS

| JP | 01-174395 | 7/1989 |
|---|---|---|
| JP | 5-500905 | 2/1993 |
| JP | 05-064594 | 3/1993 |
| JP | 09-098795 | 4/1997 |
| JP | 11-042096 | 2/1999 |
| JP | 11-046788 | 2/1999 |
| WO | WO-91/16449 | 10/1991 |

OTHER PUBLICATIONS

Gunter Jung et al., Staphyloferrin A: structurally new siderophore from staphylococci, Eur. J. Biochem. 191, 65–74 (1990).

Krista Witte et al., Enzymatic Glycoprotein Syntheses: Preparation of Ribonuclease Glycoforms via Enzymatic Glycopeptide Condensation and Glycosylation, J.Am. Chem. Soc. 1997, 119, 2114–2118.

* cited by examiner

Primary Examiner—David A. Redding
(74) Attorney, Agent, or Firm—Dickstein Shapiro Morin & Oshinsky LLP

(57) ABSTRACT

A sugar chain synthesizer comprising one or more reaction columns packed with immobilized glycosyltransferase and/or glycosidase; one or more separation means, arranged downstream from the reaction columns, for separating reaction products, unreaction products and byproducts contained in the solution eluted from the reaction columns; a first pump for feeding a primer of water soluble polymer and buffer solution to the reaction columns through a first selector valve; a second pump for feeding a buffer solution and sugar nucleotide solution to any one of the reaction columns through a second selector valve; one or more circulation flow paths connecting between a flow path downstream from the separation means and a flow path upstream from each of the reaction columns; and a third selector valve, arranged between the separation means and one or more circulation flow paths, for selective connection between the separation means and a desired circulation flow path. This synthesizer ensures continuous and automatic synthesis of sugar chains even if complicated.

11 Claims, 10 Drawing Sheets

Page 1 …

SUGAR CHAIN SYNTHESIZER

FIELD OF THE INVENTION

The present invention relates to a sugar chain synthesizer for automating synthesis and separation of a sugar chain.

BACKGROUND OF THE INVENTION

A glycoconjugate in a cell plays an important role in the signal transduction and identification of cells, for example, identification of viruses, cancer cells and blood types, and clarification of sugar chain functions is considered as one of the targets of post-genome studies.

However, the method of synthesizing an oligonucleic acid and peptide has already been established, and is automated, but sugar chain synthesis method still contains many problems to be solved. Expectations are running high for establishment of sugar chain synthesis method and realization of an effective synthesizer in order to achieve successful clarification of sugar chain functions. At present, the following three sugar chain synthesis methods are practiced:

(1) Chemical synthesis
(2) Fermentation by genetically recombinant cell and microorganism
(3) Synthesis by glycosyltransferase.

According to method (1), the targeted sugar chains are synthesized sequentially while protecting a hydroxyl group other than that for chemical bonding, and reaction steps are numerous and complicated. The method (2) provides a large volume of targeted sugar, but is accompanying by subsequent complicated purification process.

The method (3) was developed to solve the problems of methods (1) and (2). It includes the method disclosed in the Japanese Laid-Open Patent Publication No. Hei 11-42096. The method (3) uses the procedure of selective synthesis by glycosyltransferase, and does not require the process of protection of a hydroxyl group, as in method (1). Further, the amount of byproducts is smaller and the purification step subsequent to synthesis is facilitated.

In recent years, easy preparation of biologically active protein has been enabled by the development of genetic recombination technology. However, a great portion of biologically active protein is glycoprotein, and a sugar chain to be bonded is different according to each host. Activity may be seriously lost or damaged.

It will be very helpful if there is a way of reforming the changed sugar chain into the original one. Physiological function and activity are expected to be improved by modification into the sugar chain different from the originally bonded one. There are two methods of modifying the sugar chain of glycoprotein, and these methods are currently practiced.

(A) Fermentation by changing the host or using the host modified by injection of glycosyltransferase gene therein
(B) Fermentation of the obtained glycoprotein using endo- or exo-glycosidase and glycosyltransferase.

According to method (A), the sugar chain to be bonded is changed but is not always changed into the desired one. To change the sugar chain into a specified one, method (B) is preferred. A method of using the transglycosylation of endoglycosidase includes the method disclosed in the Japanese Laid-Open Patent Publication No. Hei 05-64594. A method of using the transglycosylation of exo-glycosidase and glycosyltransferase includes the method disclosed in Eur. J. Biochem. 191:71–73 (1990).

However, these methods modify only the sugar residues of the non-reducing terminus at most, and fail to bring about full-scale modification of sugar chains. There is a further way of using endoglycosidase and glycosyltransferase. For example, there is a method disclosed in J. Am. Chem. Soc. 119:2114–2118 (1997). In this method, glycosyltransferase is used to extend sugar chains onto the non-reducing terminus of the N-acetyl glucosamine residue remaining on the protein subsequent to hydrolysis by endoglycosidase, thereby promoting modification into the glycoprotein bonded with sialyl Lewisxtetraose. The sugar chain bonded is the non-reducing terminus portion of the sugar chain of glycoprotein, and this method is insufficient to achieve modification of the entire sugar chain.

A sugar chain synthesizer is disclosed in the Japanese Laid-Open International Patent Publication No. Hei 05-500905.

SUMMARY OF THE INVENTION

When an actual apparatus is used to synthesize the sugar chain according to the method (3) or (B) described above, separation and purification of the product is carried out for each step, and then the next reaction is carried out. Such a batch system is adopted at present, and human aids have been indispensable to complete the entire processing.

In the apparatus disclosed in the aforementioned Japanese Laid-Open International Patent Publication No. Hei 05-500905, glycosyltransferase can be used to extend the sugar chain using the monosaccharide, oligosaccharide and glycoprotein as substrates. However, the reaction column and separation/purification means must be connected in series on a continuous basis according to the order of the sugars to be reacted. To be more specific, even if the sugars of the same type are to be reacted in repetition, the same number of reaction columns and separation/purification means as that of sugars are required. This requires a large-scale apparatus to be manufactured. Further, automatic and continuous performance of sugar chain synthesis is not mentioned in this announcement. Further, the enzyme to be used is restricted to glycosyltransferase alone; glycosidase is not used.

The object of the present invention is to provide a sugar chain synthesizer that permits easy synthesis of sugar chains.

The present invention is characterized by comprising one or more reaction columns packed with immobilized glycosyltransferase and/or glycosidase, one or more separation/purification means arranged downstream from the reaction column in order to separate reaction products, unreaction products and byproducts contained in the solution eluted from the reaction column, and a circulating flow path for repeated circulation of them on a selective basis.

In the present invention, sugar is bonded with a primer made of water-soluble polymer or is disassociated from the primer. This makes it possible to feed the sugar bonded to the primer, to the reaction column required to the intended reaction, and ensures easy synthesis of a desired sugar chain.

DETAILED DESCRIPTION OF THE PREFERRED EMBODIMENTS

[EMBODIMENT 1]

Figure 1:
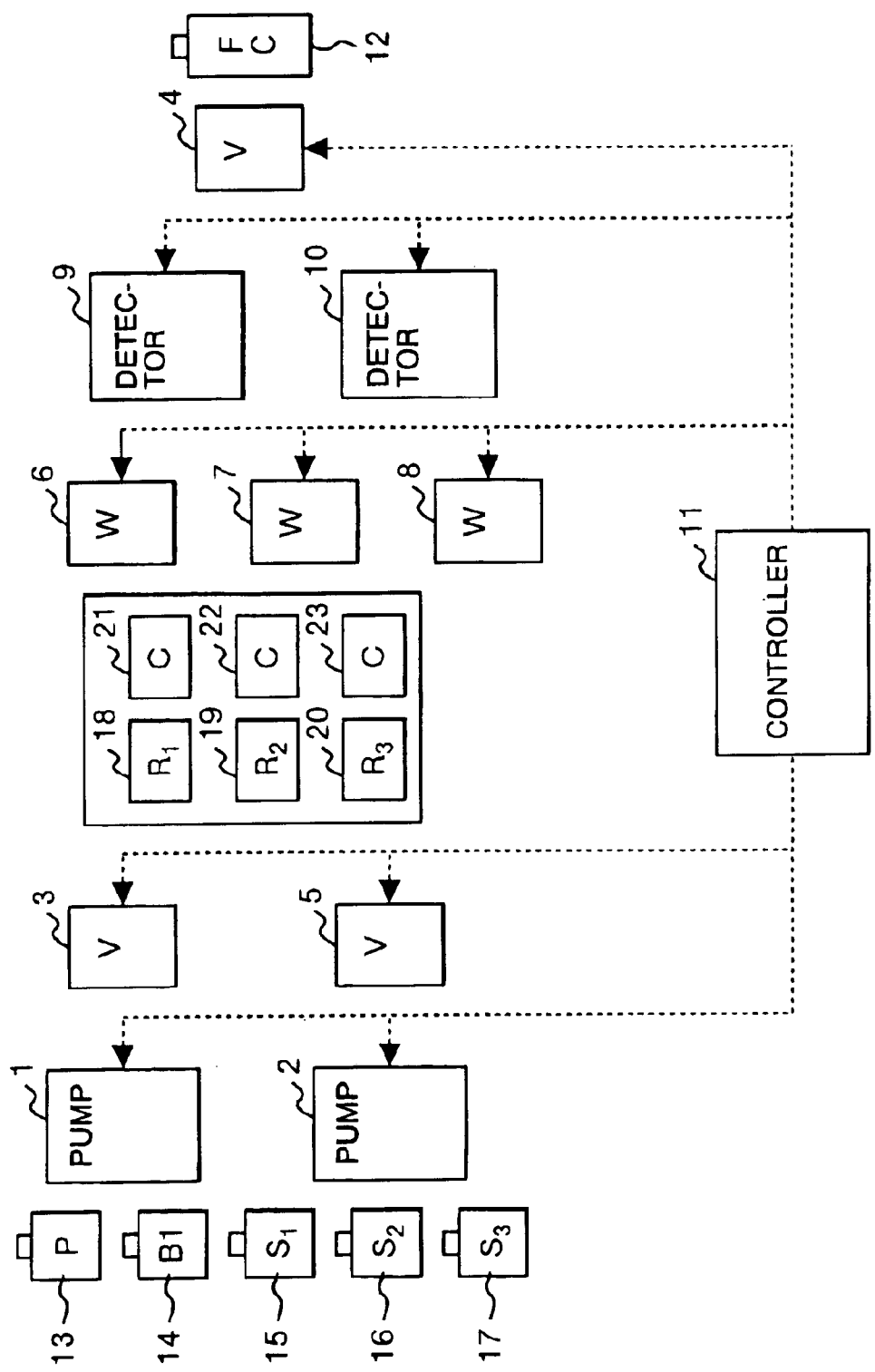
FIG. 1 is a system configuration diagram of Embodiment 1.

FIG. 1 is a system configuration diagram of Embodiment 1.

A sugar chain synthesizer comprises:

pumps 1 and 2 having the function (so-called low pressure gradient function) of selecting a plurality of solvents, and feeding the solvents while mixing these solvents with the lapse of time and changing the composition of the solvent to be fed;

six valves 3 through 8 for selecting a flow path;

reaction columns 18 through 20;

separation columns 21 through 23;

detectors 9 and 10 for detecting reaction products; and a controller 11 for controlling these components.

For example, a refractive index detector (RI), ultraviolet-visible spectrum detector (UV) or diode array absorbance detector (DAD) is used as the detector 9 used in the present apparatus in order to monitor the product. A diode array absorbance detector (DAD), mass analyzer (MS) or nuclear-magnetic resonance apparatus (NMR) is used as a detector 10 to get information on molecular structure.

Glycosyltransferase (e.g. galactosyltransferase, N-acetyl glucosaminyltransferase, N-acetyl galactosaminyltransferase, fucosyltransferase, sialyltransferase, mannosyltransferase) or glycosidase (e.g. mannosidase, galactosidase, fucosidase, sialydase, xylosidase) is immobilized and packed in the reaction column. When a column with immobilized glycosyltransferase therein is used, sugar chain can be extended by adding a new sugar thereto. If a column with immobilized glycosidase therein is used, a specified sugar can be dissociated (separated) from the sugar chain. In the present embodiment, this column is called a reaction column Rn.

Further, the reaction product refers to the primer of water soluble polymer (e.g. biological polymer such as protein, glycoprotein, glycopeptide, lipid, glycolipid, oligosaccharide or polysaccharide, or polyacrylamide derivatives disclosed in the Japanese Laid-Open International Patent Publication Nos. Hei 11-42096 and 2001-220399, with its molecular weight preferred to be 10,000 or more; "primer" hereinafter referred to as (P) and the primer is chemically bonded with sugar (Sn) hereinafter referred to as (P-Sn) in the present embodiment).

The separation column used should have a function of separating the reaction product and nucleotide, monosaccharide or oligosaccharide produced from hydrolysis. For example, such a column includes a gel filtration chromatography, cation exchange chromatography, anion exchange chromatography, affinity chromatography, dialysis and ultrafiltration.

Figure 2:
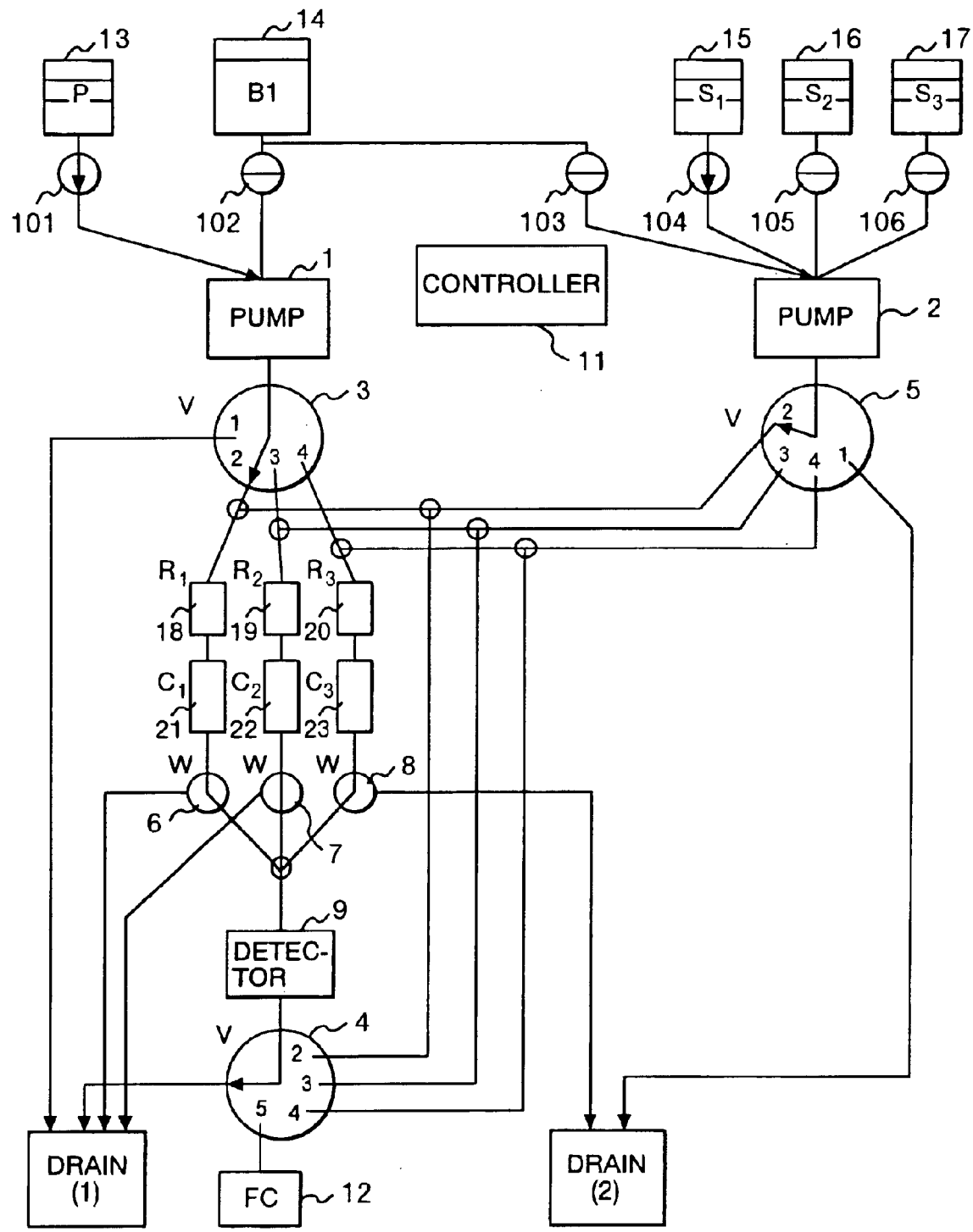
FIG. 2 is a diagram representing the flow path of a sugar chain synthesizer as Embodiment 1.

FIG. 2 is a diagram representing the flow path in the present embodiment.

Pumps 1 and 2 feed solution of bottles 13 through 17. Here the bottle 13 contains primer (P), the bottle 14 stores buffer solution, and bottles 15 through 17 incorporates sugar nucleotide solution (e.g. uridine-5'-diphosphoglactose, uridine-5'-diphospho-N-acetyl glucosamine, uridine-5'-diphospho-N-acetyl galactosamine, guanosine 5'-diphosphofucose, guanosine 5'-diphosphomannose, cytidine-5'-monophospho-N-acetylneuraminic, etc.; hereinafter referred to as "Xn-Sn" in the present embodiment).

Each bottle is assigned with solenoid valves 101 through 106 incorporated in the pump, and the solution for which the valve is opened is fed by the pump. Further, a bottle 12 is a fraction collecting bottle (FC: fraction collector), and drains (1) and (2) are drain bottles.

The following describes the operation of this apparatus with reference to FIG. 2:

Assume that primer P and sugars $S_1$, $S_2$ and $S_3$ are bonded in the sequence of $P-S_1-S_2-S_3$. Also assume that the reaction column used is the one packed with immobilized glycosyltransferase therein. In practice, however, there is no restriction to the sequence of $P-S_1-S_2-S_3$. The sequence of $P-S_1-S_2-S_1-S_3$ is also acceptable.

However, when the same type of sugar is repeated as in $P-S_1-S_1$, bottle 16 or 17 is replaced by the one containing sugar nucleotide $X_1-S_1$, and the reaction 19 or 20 is replaced by $R_1$. Alternatively, another flow path is added; namely, reaction columns and separation means (hereinafter referred to as "separation column") are extended in four rows. This also applies to the case where $S_2$ (or $S_3$) is repeated continuously.

Further, when sugar is subjected to dissociation, a column packed with immobilized glycosidase therein is added to reaction columns. When the column packed with immobilized glycosidase therein is used for processing, there is no need of using sugar nucleotide solution.

When reaction is made in the order of $P-S_1-S_2-S_3$, the present apparatus basically comprises the following ten steps:

Step 1: Injection of primer (P) and sugar nucleotide $(X_1-S_1)$ into the reaction column 18 ($R_1$) and their reaction Step 2: Separation of primer (P-$S_1$), unreacted sugar nucleotide ($X_1-S_1$) and nucleotide ($X_1$) as a reaction byproduct by the separation column 21 ($C_1$)

Step 3: Injection of primer (P-$S_1$) and nucleotide ($X_2-S_2$) into reaction column 19 ($R_2$)

Step 4: Reaction between primer (P-$S_1$) and nucleotide ($X_2-S_2$) and washing of the separation column 21 ($C_1$)

Step 5: Separation of primer (P-$S_1-S_2$), unreacted sugar nucleotide ($X_2-S_2$) and nucleotide ($X_2$) as a reaction byproduct by the separation column 21 ($C_2$)

Step 6: Injection of primer (P-$S_1-S_2$) and sugar nucleotide ($X_3-S_3$) into reaction column 20 ($R_3$)

Step 7: Reaction between primer (P-$S_1-S_2$) and sugar nucleotide ($X_3-S_3$) and washing of the separation column 22 ($C_2$)

Step 8: Separation of primer (P-$S_1-S_2-S_3$), unreacted sugar nucleotide ($X_3-S_3$) and nucleotide ($X_2$) as a reaction byproduct by the separation column 22 ($C_3$)

Step 9: Fractionation of primer (P-$S_1-S_2-S_3$) (FC)

Step 10: Washing of separation column 23 ($C_3$).

The following describes the details of each step with reference to FIG. 2: Table 1 shows the positions of valves in each step.

TABLE 1

(EMBODIMENT 1)

| Valve | 1 (1) Injection | 2 (2) Reaction | 2 Separation | 3 (1) Injection | 3 (2) Reaction | 4 Washing | 5 Separation | 6 (1) Injection | 6 (2) Reaction | 7 Washing | 8 Separation | 9 (1) Fractionation | 9 (2) | 10 Washing |
|---|---|---|---|---|---|---|---|---|---|---|---|---|---|---|
| Pump 1 | | | | | | | | | | | | | | |
| 101 (Primer) | Open | | | | | | | | | | | | | |
| 102 (Buffer) | | Open | Open | Open | Open | Open | Open | Open | Open | Open | Open | Open | Open | Open |
| V3 | P2 | P2 | P2 | P2 | P2 | P2 | P3 | P3 | P3 | P3 | P4 | P4 | P4 | P4 |
| Pump 2 | | | | | | | | | | | | | | |
| 103 (Buffer) | | Open | Open | | Open | Open | Open | | Open | Open | Open | Open | Open | Open |
| 104 (X1–S1) | Open | | | | | | | | | | | | | |
| 105 (X2–S2) | | | | Open | | | | | | | | | | |
| 106 (X3–S3) | | | | | | | | Open | | | | | | |
| V3 for fractionation | P2 | P2 | P2 | P3 | P3 | P3 | P3 | P4 | P4 | P4 | P4 | P4 | P4 | P4 |
| V4 Before detector | P1 | P1 | P1 | P3 | P1 | P1 | P1 | P4 | P1 | P1 | P1 | P5 | P1 | P1 |
| W6 (Column 21) | Detect | Detect | Detect | Detect | Detect | Detect | Detect | Detect | Detect | Detect | Detect | Detect | Detect | Detect |
| W7 (Column 22) | Detect | Detect | Detect | D | Detect | Detect | Detect | Detect | Detect | Detect | Detect | Detect | Detect | Detect |
| W8 (Column 23) | Detect | Detect | Detect | Detect | Detect | Detect | Detect | D | Detect | Detect | Detect | Detect | Detect | Detect |

In Table 1, valves 101 through 106 are in the "Close" position except for "Open". Valves 3 through 5 (V) indicate the connection positions in terms of "P1" through "P4". Valves 6 through 8 (W) indicate the drain side as a detector side in terms of "D".

<Explanation of Step 1>

(1) Open the valve 101 of the pump 1 and valve 104 of the pump 2, and connect each of the valves 3 and 5 to the position (2), so that primer (P) and nucleotide ($X_1$-$S_1$) is injected into the reaction column 18 ($R_1$). The amount of instruction is determined by the flow rate and feed time as given in equations (1) and (2):

Amount of $P$ injected $(ml)$=flow rate $(ml/min.)$×time $(min.)$     [1]

Amount of $X_1$-$S_1$ injected $(ml)$=flow rate $(ml/min.)$×time $(min.)$     [2]

When the solution feed time is the same, the ratio of primer (P) to nucleotide ($X_{1\text{-}S1}$) is determined by the flow ratio. In the case of 50%/50%, for example, the flow rate of pump 1 is equal to the flow rate of pump 2.

(2) Open the valve 102 of the pump 1 and valve 103 of the pump 2, and let the buffer 14 flow at the same flow rate so that the primer (P) and sugar nucleotide ($X_1$-$S_1$) is fed into the reaction column 18 ($R_1$). Then reduce the flow rate and allow reaction to continue, for example, at the flow rate of 0 ml/min. for a certain period of time.

<Explanation of Step 2>

Upon termination of reaction, raise the pump flow rate. The primer (P-$S_1$) as a reaction product in the reaction column 18 ($R_1$), unreacted nucleotide ($X_1$-$S_1$) and nucleotide as reaction byproduct (($X_1$), which is removed sugar nucleotide ($S_1$) from sugar sugar nucleotide ($X_1$-$S_1$)) are led to the separation column 21 ($C_1$) and separated.

The following separation modes can be considered:

(a) Gel filtration: If the molecular weight of the primer (P-$S_1$) exceed the exclusion limit of the GPC column, the primer is eluted earlier than sugar nucleotide ($X_1$-$S_1$) or nucleotide ($X_1$). (Retention capacity is smaller).

(b) Anion exchange: The neutral primer (P-$S_1$) is not absorbed but the sugar nucleotide ($X_1$-$S_1$) or nucleotide ($X_1$) as anion is absorbed by the column and leaching occurs later.

(c) Cation exchange: The neutral primer (P-$S_1$) is not absorbed but the sugar nucleotide ($X_1$-$S_1$) and nucleotide ($X_1$) as anion is eluted earlier because they are ion-excluded.

(d) Ultrafiltration: The unreacted sugar nucleotide and nucleotide as a reaction byproduct, they have smaller molecular size, are filtrated and separated from the primer with larger molecular size.

The following steps are followed when the separation mode (b) is used:

<Explanation of Step 3>

(1) When the primer (P-$S_1$) has been detected by a detector 9, set the valve 4 to the position (3) of the reaction column 19 ($R_2$), and the valve 7 to the drain side. At the same time, open the valve 105 of the pump 2 and set the valve 5 to the position (3) of the reaction column 19 ($R_2$) to feed the sugar nucleotide ($X_2$-$S_2$). If the ratio of the sugar nucleotide ($X_2$-$S_2$) is 50%, set the flow rates of the pumps 1 and 2 to the same level. (Same as in step 1).

Solution is injected until the detection of primer (P-$S_1$) terminates. If the volume of the primer (P-$S_1$) is such that "the flow rate of the pumps 1 and 2×solution injection time" has exceeded "the volume of the reaction column 19 ($R_2$)" due to the expansion of the band of primer, then suspend solution injection halfway (pump flow rate=0) and allow the reaction to terminate. Then re-inject the remaining solution.

(2) When the primer (P-$S_1$) has moved to the reaction column 19 ($R_2$), set the valve 4 to the drain position (1), and set the valve 7 back to the original position. Open the valve 103, switch the solution to be fed by the pump 2 and select the buffer 14. Inject all the primer (P-$S_1$) and sugar nucleotide ($X_2$-$S_2$) to the reaction column 19 ($R_2$). After that, reduce the flow rate and continue a flow rate of 0 ml/min. for example, for a certain period of time. In this case, only the pump 2 is used to feed the buffer to the reaction column.

<Explanation of Step 4>

While the primer (P-$S_1$) and sugar nucleotide ($X_2$-$S_2$) are reacting with each other in the reaction column 19 ($R_2$), the pump 1 continues to feed buffer 14 to the separation column 21 ($C_1$). The unreacted nucleotide ($X_1$-$S_1$) and nucleotide of reaction byproduct ($X_1$) absorbed in the column are washed out of the column.

<Explanation of Step 5>

After reaction between the primer (P-$S_1$) and sugar nucleotide ($X_2$-$S_2$), set the valve 3 to the position (3). Increase the flow rate of the buffer 14 using the pumps 1 and 2 and separate the primer (P-$S_1$-$S_2$) from the unreacted sugar nucleotide ($X_2$-$S_2$), nucleotide ($X_2$) as a reaction byproduct in the separation column 22 ($C_2$).

<Explanation of Step 6>

(1) When the primer (P-$S_1$-$S_2$) has been detected by the detector 9, set the valve 4 to the position (4) and the valve 8 to the drain position (2). At the same time, set the valve 5 to the position (4) to feed the sugar nucleotide ($X_3$-$S_3$). If the sugar nucleotide ($X_3$-$S_3$) has a ratio of 50%, set the flow rates of the pumps 1 and 2 to the same level. (Same as in step 1). Solution is injected until the detection of the primer (P-$S_1$-$S_2$) terminates.

(2) When the primer (P-$S_1$-$S_2$) has been moved to the reaction column 20 ($R_3$), set the valve 4 to the drain position (1) and set the valve 8 to the original position. Set the pump 2 to the buffer 14, and inject all the primer (P-$S_1$-$S_2$) and sugar nucleotide ($X_3$-$S_3$) to the reaction column 20 ($R_3$). After that, use only the pump 2 to feed the buffer and reduce the flow rate. Continue a flow rate of 0 ml/min. for example, for a certain period of time.

<Explanation of Step 7>

While the primer (P-$S_1$-$S_2$) and sugar nucleotide ($X_3$-$S_3$) are reacting with each other in the reaction column 20 ($R_3$), the pump 1 continues to feed buffer 14 to the separation column 22 ($C_3$). The unreacted nucleotide ($X_2$-$S_2$) and nucleotide of reaction byproduct ($X_2$) absorbed in the column are washed out of the Column.

<Explanation of Step 8>

After reaction between the primer (P-$S_1$-$S_2$) and sugar nucleotide ($X_3$-$S_3$) set the valve 3 to the position (4). Increase the flow rate of the buffer 14 using the pumps 1 and 2 and separate the water-soluble polymer (P-$S_1$-$S_2$-$S_3$) from the unreacted sugar nucleotide ($X_3$-$S_3$) and nucleotide ($X_3$) as a reaction byproduct in the separation column 23 ($C_3$).

<Explanation of Step 9>

(1) When the primer (P-$S_1$-$S_2$-$S_3$) has been detected by the detector 9, set the valve 4 to the fractionation position (5) and fractionate the sugar chain compound into the bottle 12 (FC).

(2) When detection by the detector 9 has terminated, set the valve 4 back to the drain position (1).

<Explanation of Step 10>

The pumps 1 and 2 continue to feed buffer 14 to the separation column 23 ($C_3$). The unreacted nucleotide ($X_3$-$S_3$) and nucleotide of reaction byproduct ($X_3$) absorbed in the column are washed out of the column.

The aforementioned explanation refers to the procedure for creating the synthesized sugar chain (P-$S_1$-$S_2$-$S_3$) in the present embodiment.

Figure 3:
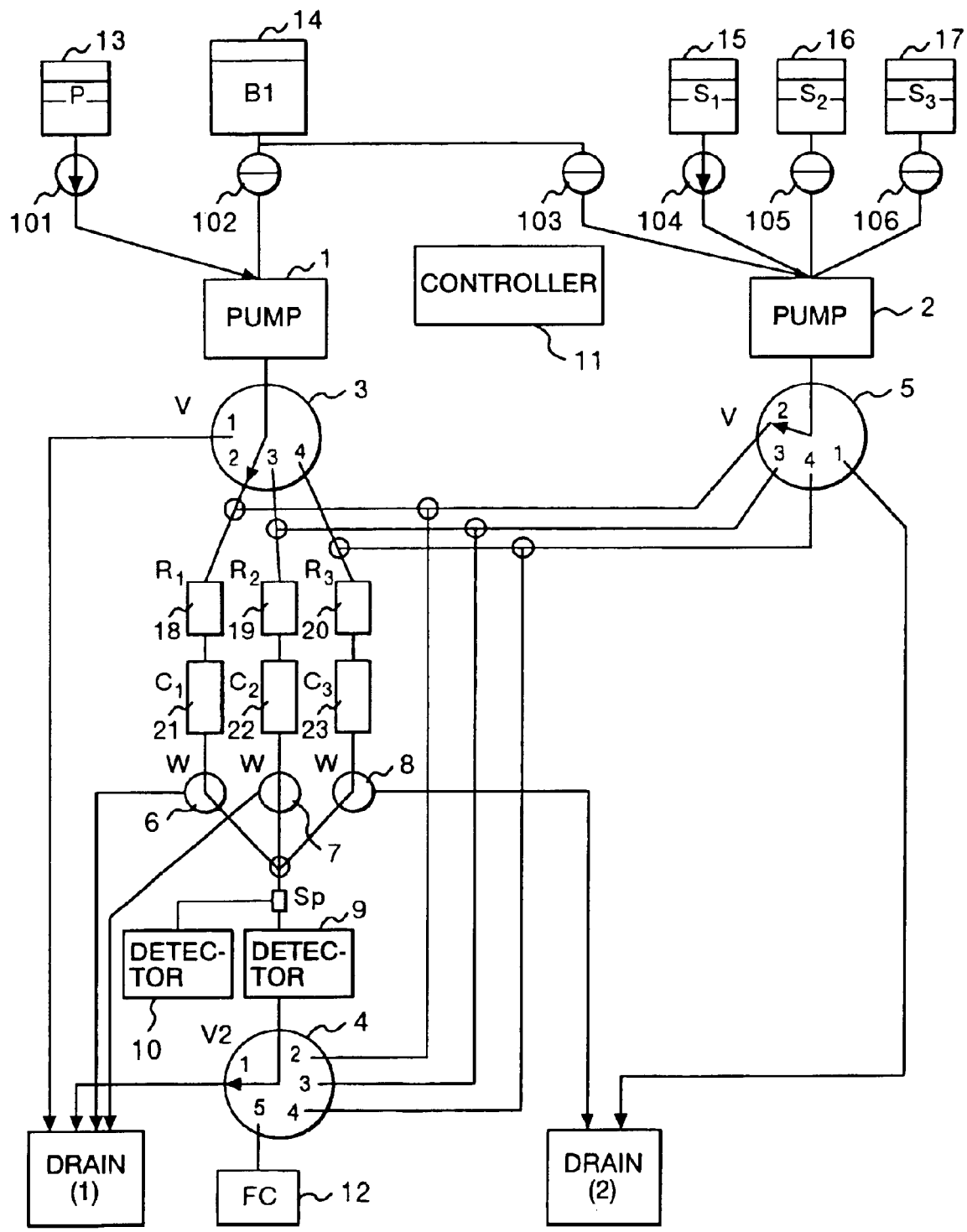
FIG. 3 is a diagram representing a variation of Embodiment 1.

FIG. 3 is a diagram representing a variation of the present embodiment. It shows the flow path when a detector 10 is added. The detector 10 is connected upstream from the detector 9 via the splitter (Sp), and captures the molecular structure of the component eluted from each separation column. The procedure for synthesizing the sugar chain In FIG. 3 is the same as that in FIG. 2.

According to the configuration given in FIG. 3, there is a detector 10 provided for detecting the information on the molecular structure of the reaction product. This makes it possible to check for each detector to see if synthesis reaction is carried out as planned or not. If reaction yield fails to reach the expected level, the next reaction for synthesis can be suspended to prevent to waste reaction reagent and time.

In the example shown with reference to the present embodiment, the time of switching the flow path by valves is based on the result of detection by the detector 9. When planned sugar modification is to be processed and the time of passage of the solution eluted from the reaction column and separation column is known, valve switching time may be controlled according to the lapse of time, not according to the result of the detector 9.

[EMBODIMENT 2]

Figure 4:
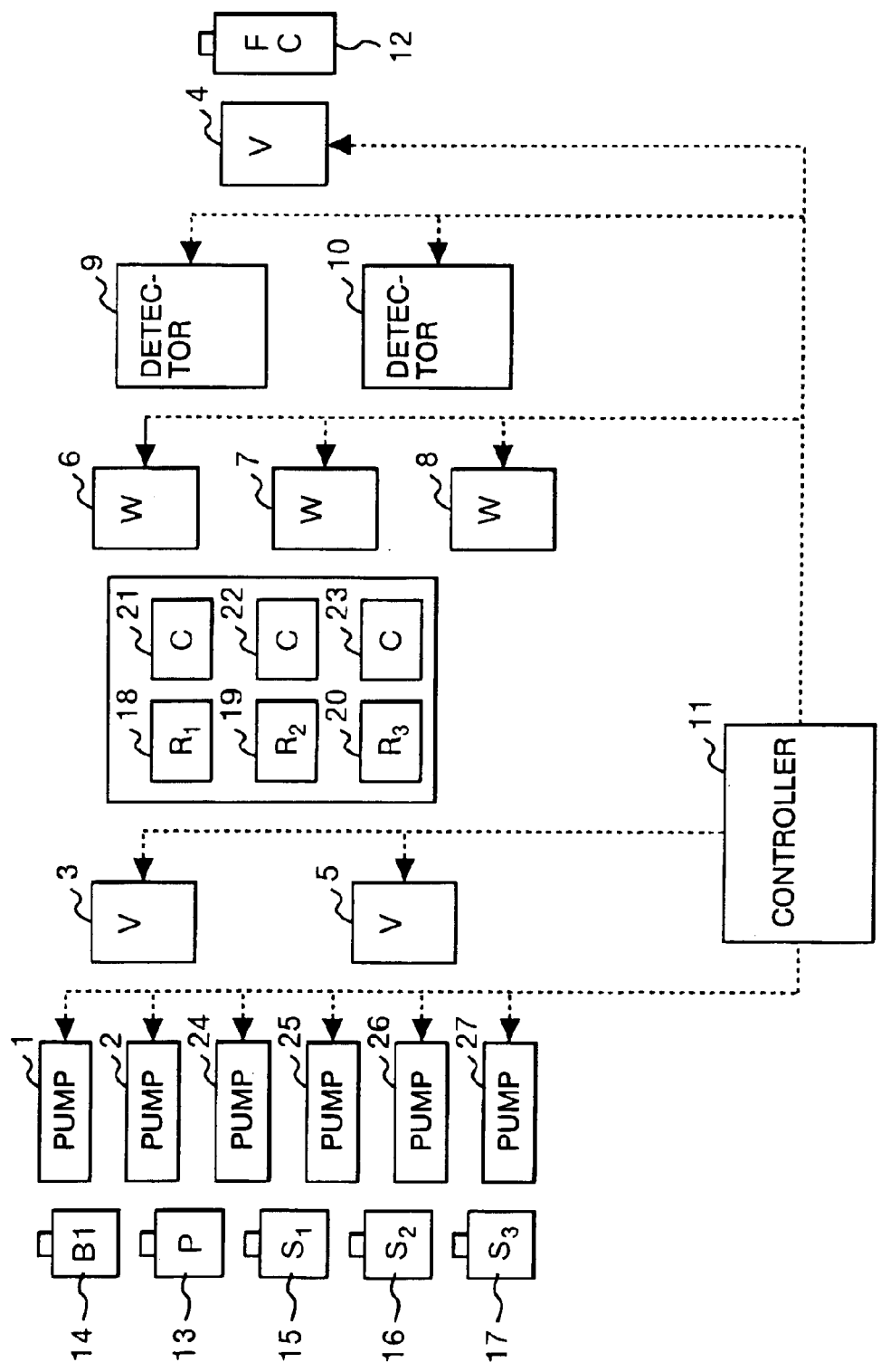
FIG. 4 is a system configuration diagram of Embodiment 2.

FIG. 4 is a system structure diagram of Embodiment 2.

The sugar chain synthesizer comprises six pumps 1, 2, 24 through 27 capable of feeding the solvents of bottles 13 through 17 at a certain flow rate for a certain time, six valves 3 through 8 for switching the flow paths, two detectors 9 and 10 for detecting the reaction product and a controller 11 for controlling these components. The detectors 9 and 10 used in the present embodiment are the same as those used in embodiment 1.

Figure 5:
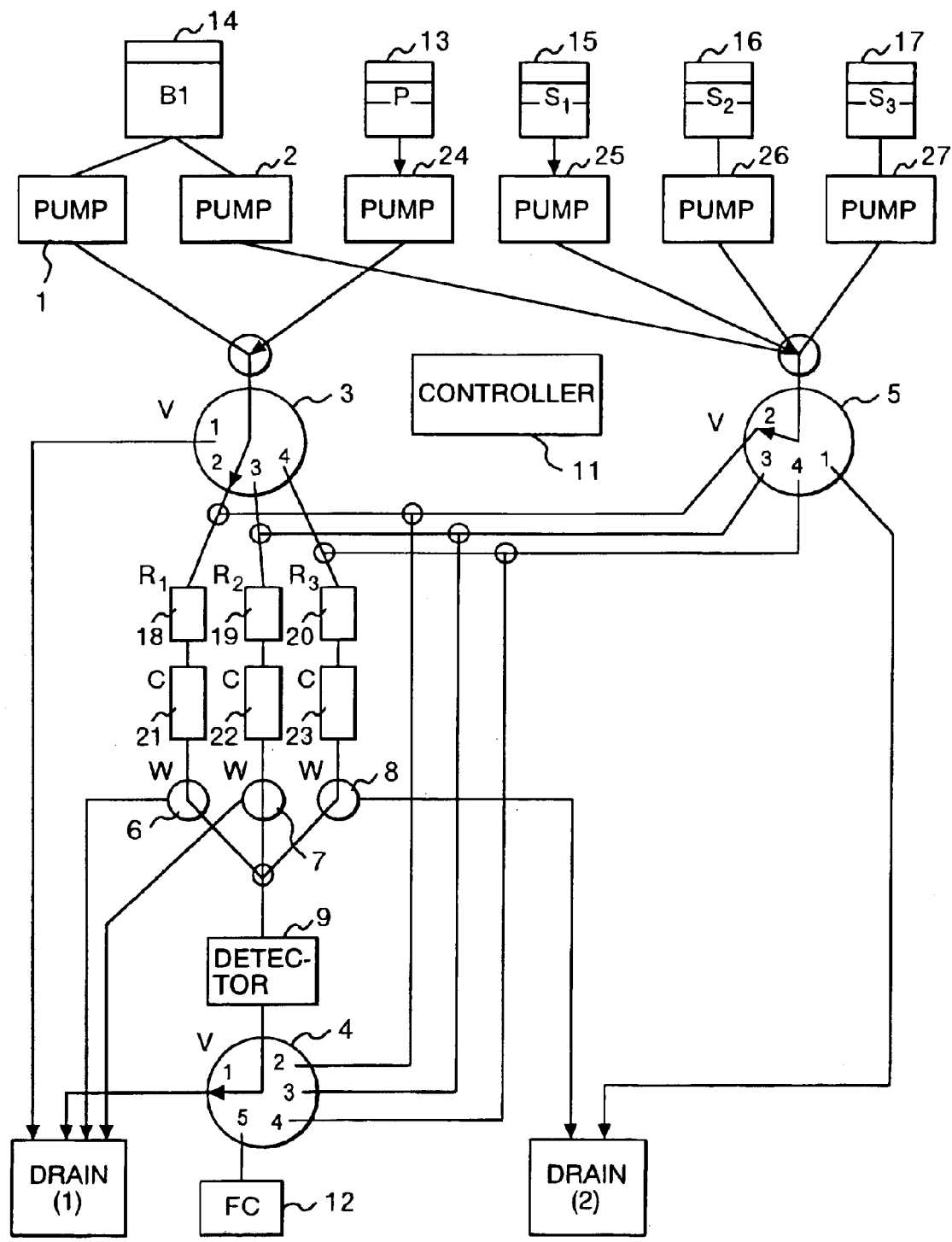
FIG. 5 is a diagram representing the flow path of a sugar chain synthesizer as Embodiment 2.

FIG. 5 is a diagram representing the flow path of a sugar chain synthesizer as Embodiment 2. This flow path shown in FIG. 5 in the one when one detector is used. The six pumps 1, 2, 24 through 27 feed the solution of bottles 13 through 17 at a certain flow rate for a certain period of time according to the control by the controller 11. The difference from the embodiment 1 is that sugar nucleotides ($X_1$-$S_1$, $X_2$-$S_2$ and $X_3$-$S_3$) are fed directly to the reaction columns 18 through 20 ($R_1$, $R_2$ and $R_3$) by the pumps 25, 26 and 27, respectively.

In the present embodiment, the pumps 1 and 2 perform the function of sending the same buffer 14 alone; so-called low-pressure gradient function is not necessary. Further, the pumps 25, 26 and 27 can feed the sugar nucleotide solutions ($X_1$-$S_1$), ($X_2$-$S_2$) and ($X_3$-$S_3$) to the reaction columns 18 through 20 without passing through respective solenoid valves. Accordingly, unlike the low-pressure gradient function where open/close operation of the solenoid valves is synchronized with the pump suction process, it is possible to provide more accurate control of the time of feeding the primer (P) and sugar nucleotide solutions ($X_1$-$S_1$), ($X_2$-$S_2$) and ($X_3$-$S_3$).

[EMBODIMENT 3]

Figure 6:
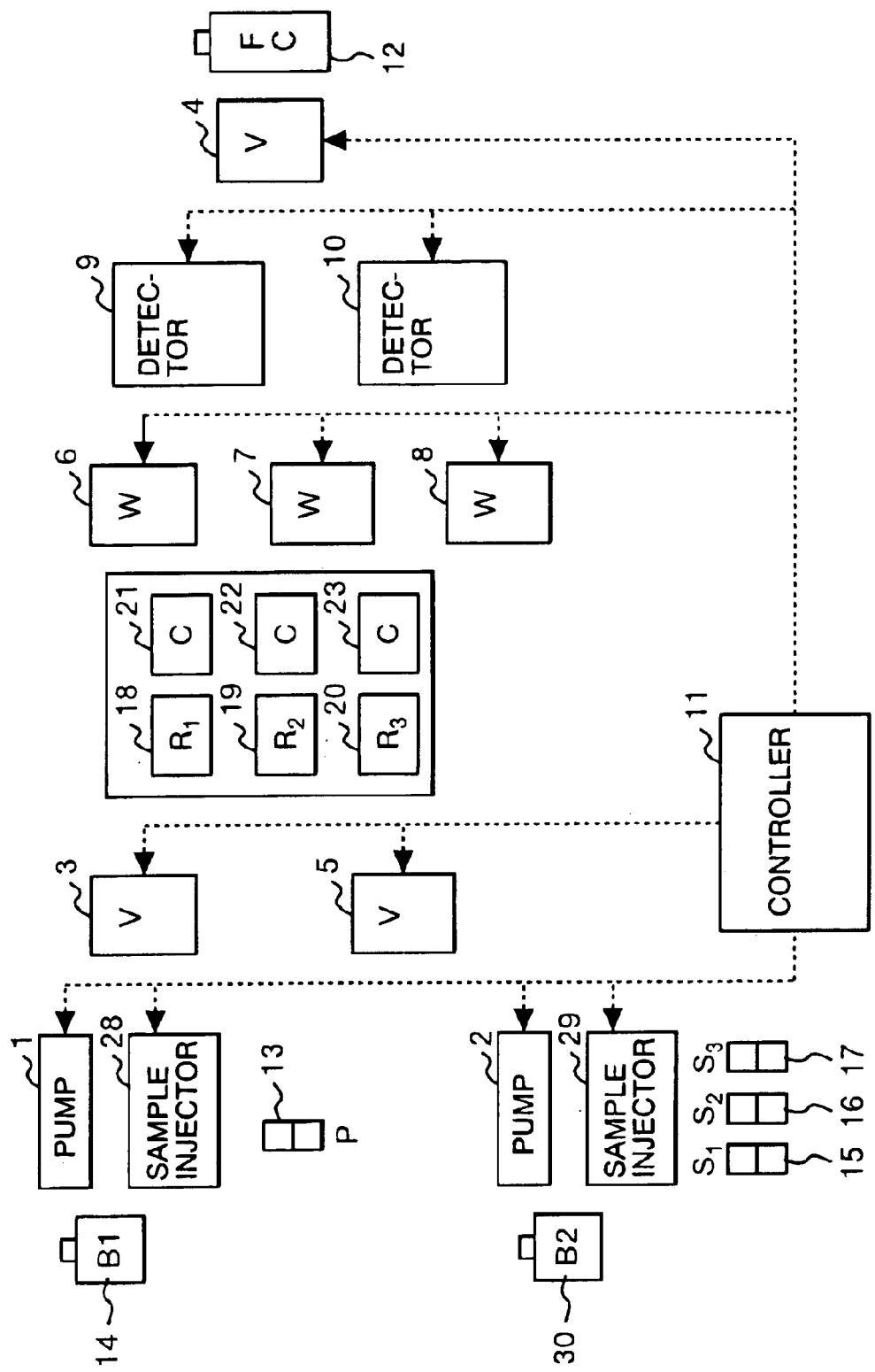
FIG. 6 is a system configuration diagram of Embodiment 3.

FIG. 6 is a system structure diagram of Embodiment 3; The sugar chain synthesizer comprises:

two pumps 1 and 2 capable of feeding the buffers (B1 and B2) 14 and 30 at a certain flow rate for a certain time;

a sample injector 28 for injecting the primer (P) 13 into a flow path;

a sample injector 29 for injecting the sugar nucleotides ($X_1$-$S_1$, $X_2$-$S_2$ and $X_3$-$S_3$) 15, 16 and 17 into the flow path;

six valves 3 through 8 for switching the flow path;

two detectors 9 and 10 for detecting reaction products; and a controller 11 for controlling these components. The detectors 9 and 10 used in the present embodiment are the same as those used in embodiment 1.

Figure 7:
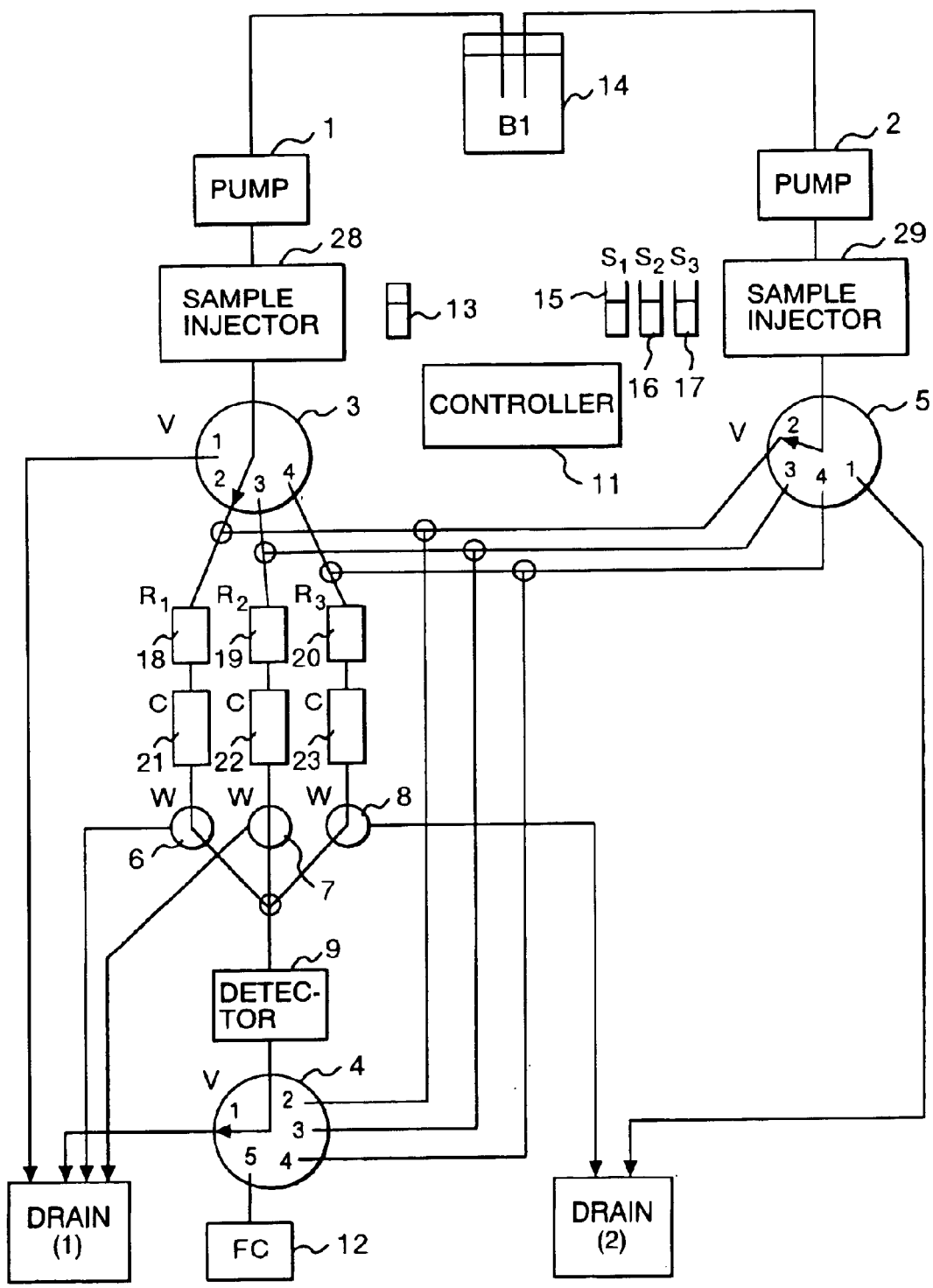
FIG. 7 is a diagram representing the flow path of a sugar chain synthesizer as Embodiment 3.

FIG. 7 is a diagram representing the flow path of a sugar chain synthesizer as Embodiment 3: This diagram shows the case where one detector is used. Two pumps 1 and 2 feed the solution of the buffers 14 and 30 (need not always be arranged for each pump; one common buffer may be sufficient as shown in FIG. 7) at a certain flow rate for a certain period of time according to the control by the controller 1. The difference from the Embodiment 1 is that the primer (P) and sugar nucleotides ($X_1$-$S_1$, $X_2$-$S_2$ and $X_3$-$S_3$) are injected into the flow path through the sample injectors 28 and 29 and are fed into the reaction columns 18, 19 and 20 ($R_1$, $R_2$ and $R_3$) by the buffer 14 (or 30).

In the present embodiment, pumps 1 and 2 are feed only the buffer 14 or 30, without the need of using a so-called low-pressure gradient function. Further, a required amount of the primer (P) and sugar nucleotides ($X_1$-$S_1$, $X_2$-$S_2$ and $X_3$-$S_3$) are injected into the flow path through the sample injection. Accordingly, unlike the case of a low-pressure gradient function where the open/close operation of the solenoid valve is synchronized with the pump suction, the present embodiment provides the advantage of eliminating the waste of the primer (P) and sugar nucleotides ($X_1$-$S_1$, $X_2$-$S_2$ and $X_3$-$S_3$).

[EMBODIMENT 4]

Figure 8:
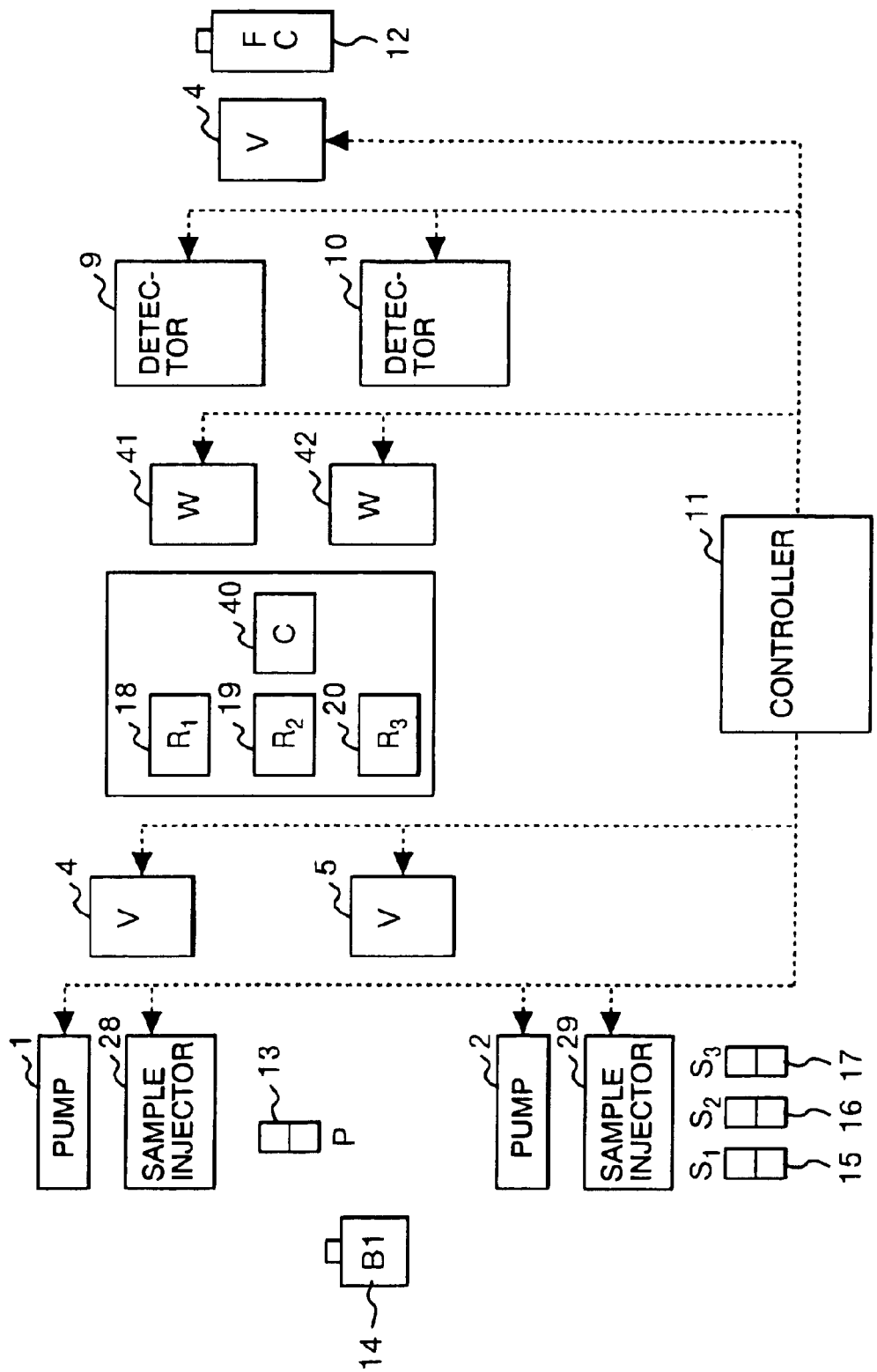
FIG. 8 is a system configuration diagram of Embodiment 4.
Figure 9:
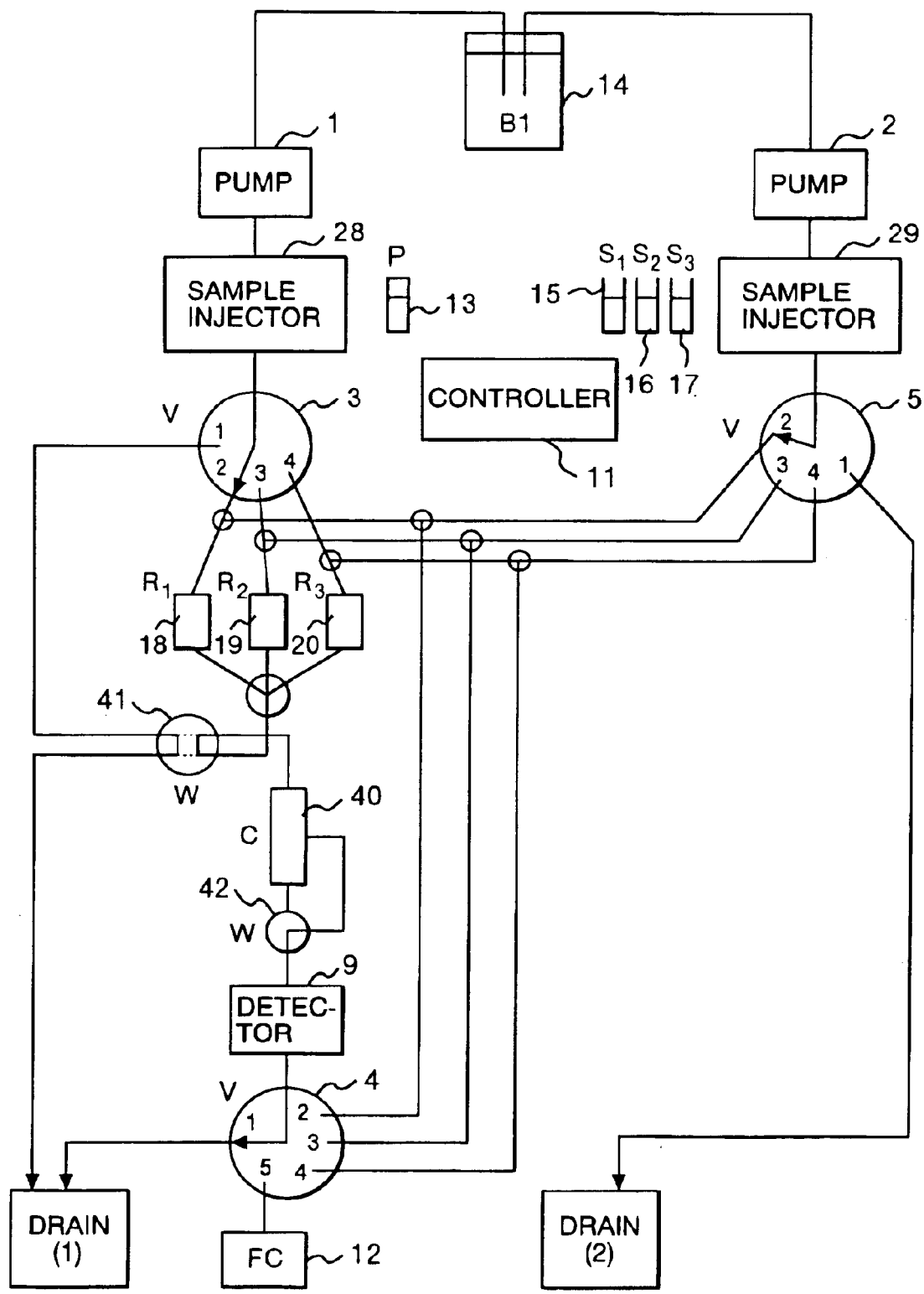
FIG. 9 is a diagram representing the flow path of a sugar chain synthesizer of Embodiment 4.

FIG. 8 is a system configuration diagram of Embodiment 4. FIG. 9 is a diagram representing the flow path. In the present embodiment, either one or two detectors may be used. When the analysis time is known in advance, control may be carried out without using a detector.

The difference from the Embodiment 3 is that the separation columns and valves connected in series to respective reaction columns in Embodiment 3 are connected centrally to one separation column, and an ultrafiltration column 40 is used for the separation column in the present embodiment.

Shared use of the separation column allows a valve 41 to be arranged instead of valves 6 through 8 in the present invention.

Figure 10:
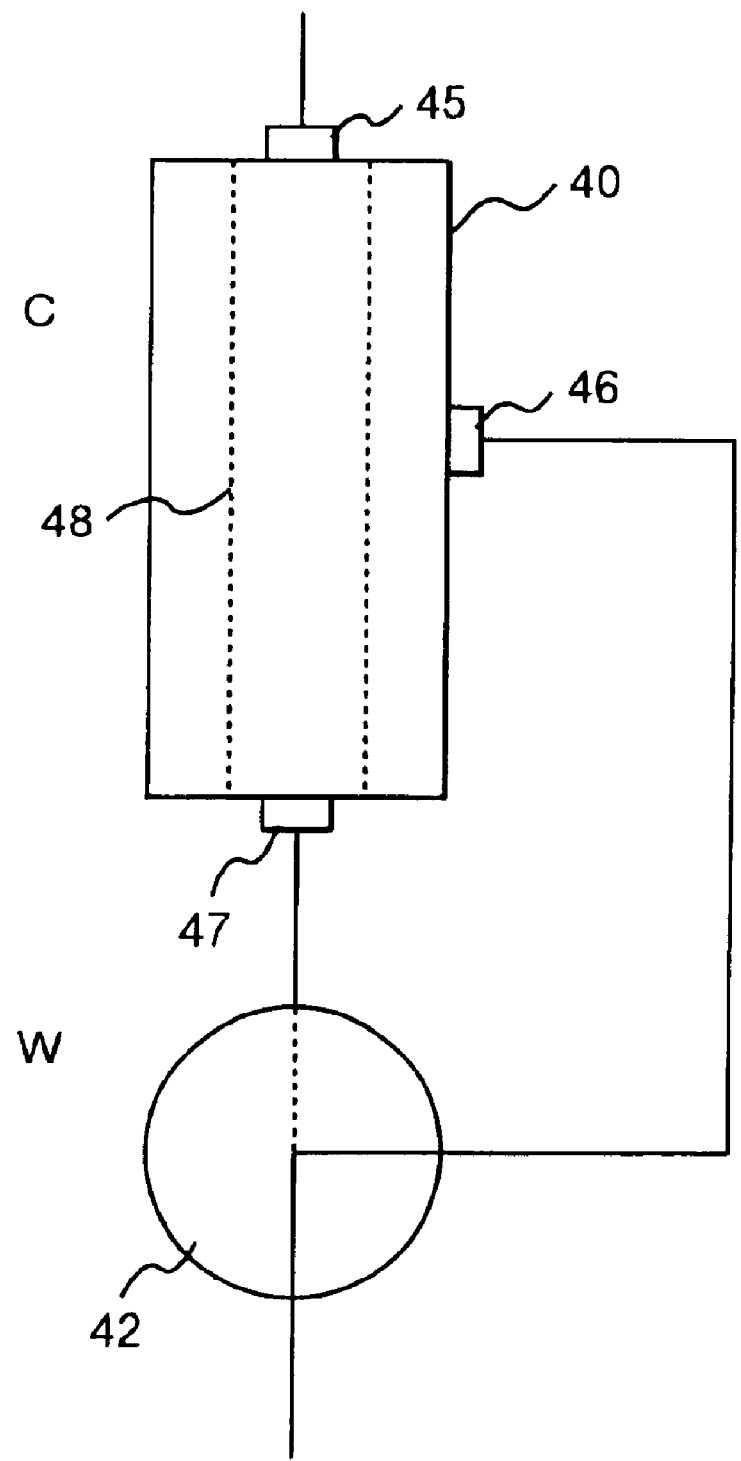
FIG. 10 is a diagram representing an example of the configuration of an ultrafiltration column.

The configuration of the ultrafiltration column 40 is given in FIG. 10. The ultrafiltration column 40 has a cylindrical ultrafiltration membrane 48 inside and two outputs; an outlet 47 for discharging the solution, injected through an inlet 45, of such a great molecular weight that they cannot pass through the membrane, and an outlet 46 for discharging the solution that has passed through the membrane. Such a membrane that allows the sugar nucleotide or nucleotide to pass by but not the primer is selected as an ultrafiltration membrane 48. The molecular weight of the primer is about 10,000 or more and that of the sugar nucleotide or nucleotide is about 400 or more. Such a considerable difference in size ensures easy separation between them.

A three-way valve 42 is arranged downstream from the outlet 47. This valve is designed to permit selective connection between the flow path on the detector side and one of the outlets 46 and 47. For the outlet on the non-connection side, the flow path is closed by the valve.

The following describes the method of separation by the ultrafiltration column 40: When the solution eluted from the reaction column has been injected, the three-way valve 42 is set to the outlet 46. Only the solution having passed through the ultrafiltration membrane 48 is discharged. The primer and sugar bonded with the primer are left in the ultrafiltration membrane 48. When the three-way valve 42 is switched over to the outlet 47 side after the lapse of the specified time, the primer and sugar having bonded with the primer are discharged to the detector side.

The operation in the present embodiment is basically the same as that shown in reference to Embodiment 1. Use of the separation column is shared. The moment when the valves 6 through 8 in the Embodiment 1 are switched over to the drain side, the valve 41 is switched over the flow path on the side of the dotted line. This arrangement permits the same operation as that of the Embodiment 1, despite shared use of the separation column.

In the Embodiment 1, shared use of the separation column allows the configuration of the apparatus to be simplified. Further, use of the ultrafiltration column as a separation column causes the primer (P) to be concentrated in the ultrafiltration column. This eliminates the problem of expansion of the band of the primer (P) as described in the step 3 of the Embodiment 1, and facilities the injection into the next reaction column.

As described above, the present invention ensures easy sugar chain synthesis even in the case of complicated sugar chain synthesis.

INDUSTRIAL FIELD OF APPLICATION

Application of the present invention to a sugar chain synthesizer facilitates synthesis or separation of sugar chains.

What is claimed is:

1. A sugar chain synthesizer comprising:

one or more reaction columns packed with immobilized glycosyltransferase and/or glycosidase;

one or more separation means, arranged downstream from said reaction columns, for separating reaction products, unreaction products and byproducts contained in the solution eluted from said reaction columns;

a first pump for feeding a primer of water-soluble polymer and buffer solution to said reaction columns through a first selector valve;

a second pump for feeding a buffer solution and sugar nucleotide solution to any one of said reaction columns through a second selector valve;

one or more circulation flow paths connecting between a flow path downstream from said separation means and a flow path upstream from each of said reaction columns; and a third selector valve, arranged between said separation means and one or more circulation flow paths, for selective connection between said separation means and a desired circulation flow path.

2. The sugar chain synthesizer according to claim 1 characterized in that said third selector valve is connected with a fractionation flow path for fractionating reaction products.

3. The sugar chain synthesizer according to claim 1 characterized in that said first and second pumps comprises a plurality of solenoid valves for feeding solutions by open/close operation and a low-pressure gradient function, and bottles containing said solutions are connected to said solenoid valves, respectively.

4. The sugar chain synthesizer according to claim 1 characterized in that a pump for feeding each of solutions to said first or second valve is arranged for each of the bottles containing a primer of water soluble polymer, buffer solution and sugar nucleotide solution.

5. The sugar chain synthesizer according to claim 1 characterized in that a first sample injector for introducing a primer of water soluble polymer, in the flow path between said first pump and said first selector valve, and a second sample injector for introducing a sugar nucleotide solution, in the flow path between said second pump and said second selector valve.

6. The sugar chain synthesizer according to claim 1 characterized in that a detector for detecting solution eluted from said one or more separation means is arranged downstream from said one or more separation means, and said detector is any one of a refractive index detector (RI), ultraviolet-visible spectrum detector (UV) or diode array absorbance detector (DAD).

7. The sugar chain synthesizer according to claim 6 characterized in that a splitter for splitting said flow path is provided in the flow path between said one or more separation means and said detector, and said splitter is connected with a second detector capable of detecting the molecular structure of eluate.

8. The sugar chain synthesizer according to claim 7 characterized in that any one of a diode array absorbance detector (DAD), mass spectrometer (MS) or nuclear magnetic resonance apparatus (NMR) is used as said second detector.

9. The sugar chain synthesizer according to claim 1 characterized in that any one of gel filtration chromatography, cation exchange chromatography, anion exchange chromatography, affinity chromatography and ultrafiltration is used as said one or more separation means.

10. The sugar chain synthesizer according to claim 1 characterized in that, when a plurality of said reaction columns are equipped and one or more separation means is provided downstream from each reaction column, a fourth valve for selective switching between:

a flow path connecting between said separation means and said third selector valve; and a flow path connecting between said separation means and drain is equipped downstream from said separation means.

11. The sugar chain synthesizer according to claim 1 characterized in that, when a plurality of said reaction columns are equipped and solution eluted from each reaction column is injected into one of said one or more separation means, a fifth valve is equipped between said reaction column and said separation means in order to provide selective switching between:

a first state for forming a flow path connecting between said reaction column and said separation means and a flow path connecting between said first valve and drain; and a second state for forming a flow path connecting between said first valve and said separation means and a flow path connecting between said reaction column and drain.

* * * * *